(12) United States Patent
Zhang et al.

(10) Patent No.: US 10,286,140 B2
(45) Date of Patent: May 14, 2019

(54) CENTRIFUGE APPARATUS FOR SEPARATING BLOOD COMPONENTS

(71) Applicant: Shanghai Jiao Tong University Affiliated Sixth People's Hospital, Shanghai (CN)

(72) Inventors: Changqing Zhang, Shanghai (CN); Ting Yuan, Shanghai (CN)

(73) Assignee: SHANGHAI JIAO TONG UNIVERSITY AFFILATED SIXTH PEOPLE'S HOSPITAL, Shanghai (CN)

( * ) Notice: Subject to any disclaimer, the term of this patent is extended or adjusted under 35 U.S.C. 154(b) by 0 days.

(21) Appl. No.: 15/138,265

(22) Filed: Apr. 26, 2016

(65) Prior Publication Data
US 2016/0325277 A1 Nov. 10, 2016

(30) Foreign Application Priority Data
May 7, 2015 (CN) .................... 2015 2 0292905 U

(51) Int. Cl.
*B01L 3/00* (2006.01)
*A61M 1/36* (2006.01)
(Continued)

(52) U.S. Cl.
CPC ........ *A61M 1/3693* (2013.01); *A61M 1/0272* (2013.01); *B01D 21/245* (2013.01);
(Continued)

(58) Field of Classification Search
CPC .. B01L 3/52; B01L 3/561; B01L 3/567; B01L 3/5082; B01L 3/50825;
(Continued)

(56) References Cited

U.S. PATENT DOCUMENTS 4,464,340 A * 8/1984 Lennox, Jr. ............. B01L 3/508
251/63
8,734,736 B2 * 5/2014 Ludwig ................... B01L 3/567
137/247
(Continued)

FOREIGN PATENT DOCUMENTS

CN 2721094 Y 8/2005

*Primary Examiner* — Brian R Gordon
(74) *Attorney, Agent, or Firm* — Heslin Rothenberg Farley & Mesiti P.C.

(57) ABSTRACT

A centrifuge apparatus for separating blood components includes a centrifuge tube and a flow dividing mechanism, and the flow dividing mechanism is fixed at the bottom of the centrifuge tube. Moreover, the bottom of the centrifuge tube is further provided with a discharge hole. The flow dividing mechanism includes an adjustable flow divider valve and a flow guiding channel, and the adjustable flow divider valve is configured to adjust relative positions of the flow guiding channel and the discharge hole, thereby implementing flow division of blood components at the bottom layer of the centrifuge tube. The centrifuge apparatus can be used to manufacture platelet-rich plasma in a convenient and simple way, and can improve the clinical operation efficiency. Moreover, the centrifuge apparatus may completely avoid the possibility of introducing pollution into a sample during the manufacturing, thereby improving the preciseness and stability of manufacturing the platelet-rich plasma.

8 Claims, 2 Drawing Sheets

(51) Int. Cl.
  *B01D 21/26* (2006.01)
  *A61M 1/02* (2006.01)
  *B01D 21/24* (2006.01)
  *B01D 21/34* (2006.01)
  *G01N 33/49* (2006.01)

(52) U.S. Cl.
  CPC ........... *B01D 21/262* (2013.01); *B01D 21/34* (2013.01); *B01L 3/5021* (2013.01); *A61M 2202/0427* (2013.01); *B01L 2200/026* (2013.01); *B01L 2400/0622* (2013.01); *B01L 2400/0644* (2013.01); *G01N 33/491* (2013.01)

(58) Field of Classification Search
  CPC ............... B01L 3/5021; B01L 3/50215; B01L 2200/026; B01L 2400/0622; B01L 2400/0638; B01L 2400/0644; B01L 2400/0655
  See application file for complete search history.

(56) References Cited

U.S. PATENT DOCUMENTS

2004/0213699 A1* 10/2004 Berndtsson ............. B01L 3/502
                                                    422/549
2011/0081281 A1*  4/2011 Ludwig ................... B01L 3/567
                                                    422/509
2015/0080204 A1*  3/2015 Kassis ................... B01L 3/5021
                                                    494/37
2017/0014819 A1*  1/2017 U'Ren ................ B01L 3/50215

* cited by examiner

CENTRIFUGE APPARATUS FOR SEPARATING BLOOD COMPONENTS

CROSS REFERENCE TO RELATED APPLICATIONS

The present application claims priority from Chinese utility model application number CN201520292905.0 filed on May 7, 2015, which is hereby incorporated herein by reference in its entirety.

TECHNICAL FIELD

The present application relates to the field of medical centrifuge tube technologies, and in particular, to a centrifuge apparatus for separating blood components.

BACKGROUND

Platelet-rich plasma (PRP) is a platelet concentrate extracted from body blood through centrifugation, and contains high-concentration concentrate, leukocyte and fibrous protein. Various growth factors may be seen after the platelet is activated: the leukocyte may prevent the infection, and the fibrous protein can locally construct three-dimensional structures that are necessary for repairing tissues. Concentrated PRP components can not only provide "concentrated nutrition" for tissue reparation, but also establish a better reparation environment for tissue reparation. A large amount of fundamental researches and clinical experiments have proved that the PRP can significantly improve reparation of bone tissues and soft tissues. As the PRP is autologous, safe and efficient, it has been gradually widely applied in clinical applications in recent years, and now has been applied to the orthopedics, oral and maxillofacial surgery, plastic surgery, cosmetology, sports medicine, neurosurgery, ophthalmology, otorhinolaryngology, and obstetrics, etc.

Currently, there are more than ten kinds of PRP manufacturing devices approved by the U.S. FDA to be applied clinically, and most of them adopt a twice-centrifugation method. However, these devices are expensive, and some devices are poor in platelet concentration and recovery of extracted PRP. Chinese domestic PRP manufacturing uses a manual open-type twice-centrifugation method; however, this method can result in a sample being contaminated, and the manufactured PRP concentration and growth factor activity are not stable. In 2004, Zhang Changqing et al. designed a centrifuge tube for manufacturing platelet-rich plasma (Pat. No.: ZL200420081020.8), and this centrifuge tube greatly improves the convenience and safety of manufacturing PRP. Thereafter, the team of Doctor Zhang and Shangdong Weigao Group Medical Polymer Co. Ltd. cooperatively develop a PRP clinical manufacturing set certificated by the State Food and Drug Administration, which is the only PRP manufacturing set approved for clinical use in China currently. However, after being widely used clinically, the set is found to have defects such as inconvenient operation and the possibility of introducing contamination during manufacturing, thereby having the possibility of affecting the preciseness and stability of manufacturing the PRP.

SUMMARY

Embodiments of the present patent application provide a centrifuge apparatus for separating blood components, and the centrifuge apparatus is convenient and easy for use in the operation, and can prevent a sample from being contaminated during operation.

To solve the above technical problem, an embodiment of the present patent application provides a centrifuge apparatus for separating blood components. The centrifuge apparatus includes a centrifuge tube and a flow dividing mechanism. The flow dividing mechanism is fixed at the bottom of the centrifuge tube. The bottom of the centrifuge tube is further provided with a discharge hole. Moreover, the flow dividing mechanism includes an adjustable flow divider valve and a flow guiding channel, and the adjustable flow divider valve is operable to adjust a relative position of the flow guiding channel and the discharge hole.

A method of manufacturing platelet-rich plasma by using the above centrifuge apparatus specifically includes the following steps: S1: the blood is extracted and injected into a centrifuge tube, and the centrifuge tube is placed into a centrifuge for centrifugation; S2: after the centrifugation, the blood is layered, and by adjusting the adjustable flow divider valve, the flow guiding channel and the discharge hole are communicated, so as to perform flow division on erythrocyte at the bottom layer of the centrifuge tube; S3: the adjustable flow divider valve is adjusted so that the flow guiding channel and the discharge hole are not communicated, the residual blood components in the centrifuge tube are shaken up, and the centrifuge tube is placed in the centrifuge for a second centrifugation; S4: after the second centrifugation, the blood is layered, and the adjustable flow divider valve is adjusted so that the flow guiding channel and the discharge hole are communicated, so as to perform flow division on platelet-rich plasma at the bottom layer of the centrifuge tube, thereby obtaining the platelet-rich plasma.

Compared with the conventional centrifuge tube for manufacturing PRP, the centrifuge apparatus provided in an embodiment of the present patent application has the following advantages: (1) an intermediate straw is removed, as the intermediate straw may have residual erythrocyte in the process of manufacturing the PRP by using centrifugation, thereby affecting the preciseness and stability of the concentration of the finally manufactured PRP; (2) a side PPP extraction hole is removed, thereby avoiding the possibility that talcum powder or bacteria fall into the centrifuge tube when extracting the PPP at the side hole; (3) all screw covers are removed, thereby further preventing the sample from being contaminated when a screw cover is unscrewed, and improving the convenience of manufacturing the PRP; and (4) the discharge hole and the flow divider apparatus are added at the bottom of the centrifuge tube, the blood is layered after the centrifugation, the component at the bottom layer flows into the flow dividing mechanism through the discharge hole, so that the blood components can be completely separated and will not be mixed, as a result, the concentration of the manufactured PRP is more precise and more stable. Therefore, the centrifuge apparatus provided in the implementation manner of the present application improves the convenience of the PRP manufacturing, can completely prevent the sample from being contaminated during the operation, and further improves the preciseness and stability of manufacturing the PRP, thereby solving various problems of the PRP manufacturing technology in clinical applications, so that it can better push the clinical applications of the PRP to enable more patients be benefited from it.

In one embodiment, in the centrifuge apparatus for separating blood components provided in the present application, a tube opening of the centrifuge tube is provided with a halogenated butyl rubber plug. During use, an injection needle is used to puncture the halogenated butyl rubber plug, and then injects a to-be-separated blood sample into the centrifuge tube; therefore, the possibility of introducing contamination in the primary operation of transferring the sample to the centrifuge tube may be avoided.

In one embodiment, in the centrifuge apparatus for separating blood components provided in the present application, the adjustable flow divider valve is a rotate-type flow divider valve or a push-type flow divider valve, that is, relative positions of the flow guiding channel and the discharge hole are adjusted by rotating or pushing the divider valve.

In one embodiment, in the centrifuge apparatus for separating blood components provided in the present application, the flow guiding channel includes a first flow guiding channel and a second flow guiding channel that are independent to each other; the adjustable flow divider valve is configured to respectively adjust relative positions of the first flow guiding channel and the discharge hole, and relative positions of the second flow guiding channel and the discharge hole. In the process of manufacturing platelet-rich plasma by using the centrifuge apparatus provided in the present application, two centrifugations are required to separate erythrocyte and platelet-rich plasma at the bottom of the centrifuge tube, and therefore, it is a preferable solution to dispose two flow guiding channels. After the two centrifugations, the erythrocyte and the platelet-rich plasma are divided through different flow guiding channels without affecting each other, it is ensured that the finally prepared platelet-rich plasma does not have an erythrocyte component mixed therein, thereby improving the concentration and purity of the platelet-rich plasma.

In one embodiment, in the centrifuge apparatus for separating blood components provided in the present application, the flow dividing mechanism further includes a first flow dividing cabin and a second flow dividing cabin. When the first flow guiding channel and the discharge hole are communicated, the first flow dividing cabin and the first flow guiding channel are also communicated, thereby implementing communication of the discharge hole, the first flow guiding channel, and the first flow dividing cabin; when the second flow guiding channel and the discharge hole are communicated, the second flow dividing cabin and the second flow guiding channel are also communicated, thereby implementing communication of the discharge hole, the second flow guiding channel, and the second flow dividing cabin. Specifically, after the first centrifugation in the process of manufacturing the PRP, the discharge hole, the first flow guiding channel and the first flow dividing cabin are communicated, so that the erythrocyte flows into the first flow dividing cabin through the discharge hole and the first flow guiding channel; and after the second centrifugation in the process of manufacturing the PRP, the discharge hole, the second flow guiding channel and the second flow dividing cabin are communicated, so that the platelet-rich plasma flows into the second flow dividing cabin through the discharge hole and the second flow guiding channel. The two flow dividing cabins respectively implement automatic collection of the erythrocyte and the platelet-rich plasma, and it is unnecessary to further disposed another apparatus for receiving a separated blood component at the exterior of the centrifuge apparatus, thereby further improving the convenience in using the centrifuge apparatus provided in the present application.

In one embodiment, in the centrifuge apparatus for separating blood components provided in the present application, the first flow dividing cabin and the second flow dividing cabin are each provided with a halogenated butyl rubber plug. After the first flow dividing cabin and the second flow dividing cabin respectively implements collection of two blood components, injection needles are used to puncture the halogenated butyl rubber plug to extract the blood components in the flow dividing cabins, thereby further avoiding the possibility of introducing contamination during the operation.

In one embodiment, in the centrifuge apparatus for separating blood components provided in the present application, the first flow dividing cabin and the second flow dividing cabin may be detachably disposed in the flow dividing mechanism. In the process of separating blood components by using the centrifuge apparatus provided in an embodiment of the present application, according to actual requirements, the first flow dividing cabin or the second flow dividing cabin may be mounted in the flow dividing mechanism, or may be removed temporarily from the flow dividing mechanism or even be replaced. By means of the detachable disposition of the flow dividing cabin, the centrifuge apparatus provided by the present application is more convenient and humanized in the process of separating blood components.

In one embodiment, in the centrifuge apparatus for separating blood components provided in the present application, the adjustable flow divider valve is provided with a limiting mechanism, and the limiting mechanism performs limiting and locking when the flow guiding channel and the discharge hole are communicated. Specifically, the limiting mechanism may select a spring steel ball that can function for positioning and locking, and may also select a limiting guide shaft. The limiting mechanism can not only guide and limit the adjustment range of the adjustable flow divider valve, but also limit the positions of the flow guiding channel and the discharge hole when the two are communicated; therefore, it is ensured that in the process of dividing the blood component, the discharge hole and the flow guiding channel together provide a stable flowing channel, so that the manufacturing process of the PRP is more precise and more stable.

In one embodiment, in the centrifuge apparatus for separating blood components provided in the present application, the adjustable flow divider valve is provided with a control hand wheel, and the control hand wheel is provided with an isolating membrane. The isolating membrane is used for isolating direct contact between the hand of an operator and the hand wheel, thereby preventing the blood sample from contaminating the hand during the operation.

BRIEF DESCRIPTION OF THE DRAWINGS

The disclosure will become more fully understood from the detailed description given herein below for illustration only, and thus are not limitative of the disclosure, and wherein.

DETAILED DESCRIPTION OF THE EMBODIMENTS

In order that objectives, technical solutions and advantages of the present application are clearer, detailed descriptions are made on various embodiments of the present application through the accompanying drawings. However, the person of ordinary skill in the art can understand that, in the embodiments of the present application, many technical details are provided for a skilled reader to better understand the present application. However, the technical solution for protection by means of the claims of the present application may also be implemented based on various variations and modifications of the embodiments even without the presence of technical details.

Figure 1:
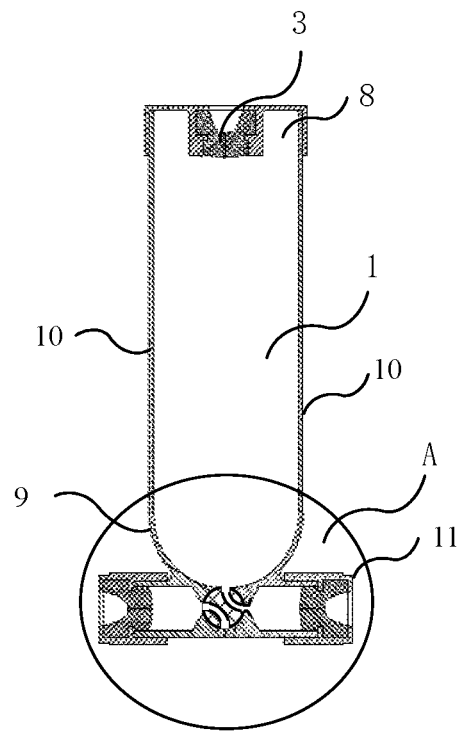
FIG. 1 is a schematic structural diagram of a centrifuge apparatus for separating blood components according to certain embodiments of the present application.
Figure 2:
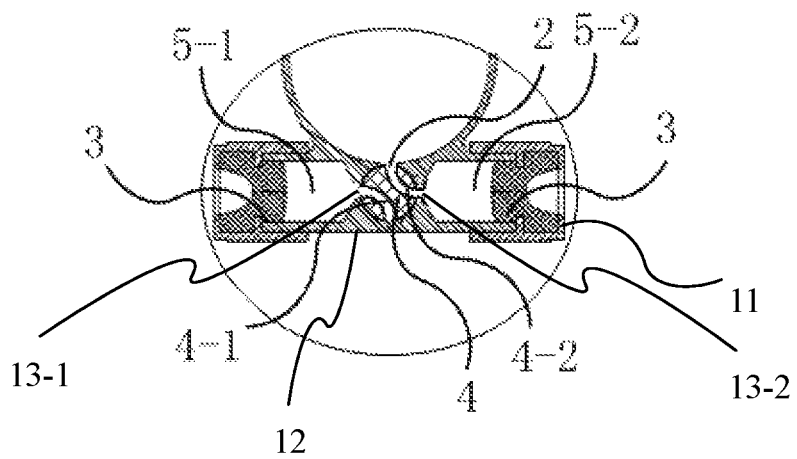
FIG. 2 is a partially enlarged diagram of a part A in FIG. 1.

Embodiments of the present application relate to a centrifuge apparatus for separating blood components, and a schematic structural diagram thereof is shown in FIG. 1, and a partial enlarged diagram of a part A (including a flow dividing mechanism) in FIG. 1 is shown in FIG. 2. Specifically, the centrifuge apparatus includes a centrifuge tube 1. A tube opening 8 at an upper end of the centrifuge tube 1 is provided with a halogenated butyl rubber plug 3. A protruding curved bottom 9 of the centrifuge tube 1 is connected to side walls 10 of the centrifuge tube and extends across and closes a lower end of the centrifuge tube. A discharge hole 2 extends through the curved bottom 9, and, in an example, the aperture of the discharge hole 2 is 1 mm; moreover, the exterior of the protruding curved bottom 9 of the centrifuge tube 1 further has a flow dividing mechanism 11 fixed thereon. The flow dividing mechanism 11 includes an outer casement 12, and an adjustable flow divider valve 4 received within an internal cavity of the flow dividing mechanism. The flow dividing mechanism 11 further includes first and second spaced apart, diametrically opposed, sideways facing outlets 13-1 and 13-2.

In a first example, the flow dividing mechanism includes a rotate-type flow divider valve 4, and a first flow guiding channel 4-1 and a second flow guiding channel 4-2 disposed in a valve body of the rotate-type flow divider valve 4. The rotate-type flow divider valve 4 is provided with a control hand wheel, and the rotate-type flow divider valve 4 may be rotated by operating the control hand wheel, so as to adjust respective positions of the first flow guiding channel 4-1 and the second flow guiding channel 4-2 relative to the discharge hole 2 (definitely, shapes of the first flow guiding channel 4-1 and the second flow guiding channel 4-2 may be varied). Specifically, by rotating and adjusting the rotate-type flow divider valve 4, the flow dividing mechanism may be in one of the following three states: 1. The first flow guiding channel 4-1 and the second flow guiding channel 4-2 are both not in communicated with the discharge hole 2; 2. the first flow guiding channel 4-1and the discharge hole 2 are communicated; and 3. the second flow guiding channel 4-2 and the discharge hole 2 are communicated.

Moreover, the flow dividing mechanism further includes a first flow dividing cabin or fluid storage chamber 5-1 and a second flow dividing cabin or fluid storage chamber 5-2. When the first flow guiding channel 4-1 and the discharge hole 2 are communicated, the first flow dividing cabin 5-1 and the first flow guiding channel 4-1 are also communicated; that is, communication between the discharge hole 2, the first flow guiding channel 4-1 and the first flow dividing cabin 5-1 is implemented. When the second flow guiding channel 4-2 and the discharge hole 2 are communicated, the second flow dividing cabin 5-2 and the second flow guiding channel 4-2 are also communicated, that is, communication between the discharge hole 2, the second flow guiding channel 4-2 and the second flow dividing cabin 5-2 is implemented. Moreover, the first flow dividing cabin 5-1 and the second flow dividing cabin 5-2 disposed in this example are also each provided with a halogenated butyl rubber plug 3-1, 3-2, respectively.

The steps of manufacturing platelet-rich plasma by using the centrifuge apparatus for separating blood components provided in this example are described as follows: S1: blood is extracted, an injection needle is used to puncture the halogenated butyl rubber plug 3 and inject the blood into the centrifuge tube 1, and the centrifuge tube 1 is placed in the centrifuge for centrifugation; S2: after the centrifugation, the blood is layered, erythrocyte is located at the bottom layer of the centrifuge tube 1, the rotate-type flow divider valve 4 is adjusted so that the flow guiding channel 4-1 and the discharge hole 2 are communicated, and in this case, the flow guiding cabin 5-1 is also communicated with the flow guiding channel 4-1, the erythrocyte at the bottom layer of the centrifuge tube 1 is divided through the discharge hole 2 and flows into the flow dividing cabin 5-1 through the flow guiding channel 4-1; S3: after the erythrocyte at the bottom layer of the centrifuge tube 1 is divided, the adjustable flow divider valve 4 is adjusted so that the discharge hole 2 is in a direction not in communication with any of the flow guiding channels, the residual blood components in the centrifuge tube Tare shaken up, the centrifuge tube 1 is then placed into the centrifuge to conduct second centrifugation; S4: after the second centrifugation, the blood in the centrifuge tube 1 is further layered, platelet-rich plasma is located at the bottom layer, the adjustable flow divider valve 4 is adjusted so that the flow guiding channel 4-2 is communicated with the discharge hole 2, and in this case, the flow guiding cabin 5-2 is also communicated with the flow guiding channel 4-2, the platelet-rich plasma at the bottom layer of the centrifuge tube 1 is divided through the discharge hole 2, and enters the flow dividing cabin 5-2 through the flow guiding channel 4-2; through observation, after the platelet-rich plasma at the bottom layer of the centrifuge tube 1 totally flows out, the rotate-type flow divider valve 4 is adjusted so that the discharge hole 2 is again in a state not in communication with any of the flow guiding channels, thereby implementing the flow division of the platelet-rich plasma. In this case, the platelet-rich plasma is totally stored in the flow dividing cabin 5-2, an injection needle is used to puncture the halogenated butyl rubber plug 3-2 and extract the platelet-rich plasma in the flow dividing cabin 5-2, thereby implementing the preparation process of the platelet-rich plasma.

The centrifuge tube used for manufacturing platelet-rich plasma provided in this example has the following advantages: there is not any structure such as a suction straw, an extraction hole and a screw cover in the whole centrifuge apparatus, and a liquid transferring operation is not involved; therefore, in the process of manufacturing the PRP, there is no operation that may introduce contamination into the sample, thereby ensuring the high purity of the PRP product. Moreover, the apparatus is provided with a dedicated flow dividing mechanism to conduct flow division on the erythrocyte and the platelet-rich plasma, and is also provided with flow dividing cabins to store the erythrocyte and the platelet-rich plasma obtained after the flow division, the preparation operation is simple and convenient, and the efficiency in the clinical use may be greatly improved.

A centrifuge apparatus for separating blood components involved in a second example is an improvement of the first example. Specifically, the two flow dividing cabins are disposed in a detachable manner.

During an actual use, when the centrifuge tube is placed into the centrifuge for centrifugation, the two flow dividing cabins are both in a detached state, and do not enter the centrifuge to participate in the centrifugation, which may improve the convenience of the centrifugation operation. After the centrifugation is completed and before the rotate-type flow divider valve is adjusted for flow division, the first flow dividing cabin or the second flow dividing cabin is mounted in the flow dividing mechanism and is in communication with a flow dividing channel; then, the blood component at the bottom layer of the centrifuge tube is divided and stored. Definitely, the operation of extracting the required platelet-rich plasma in the flow dividing cabin may also be conducted after the flow dividing cabin is removed from the flow dividing mechanism, which also further improves the operation convenience in the step of extracting the platelet-rich plasma.

Further, as a simplification, the flow dividing cabin may even not be disposed, and during the actual use, an external receiving apparatus is disposed under the flow guiding channel, thereby implementing receiving and storage of substance components divided out.

Figure 3:
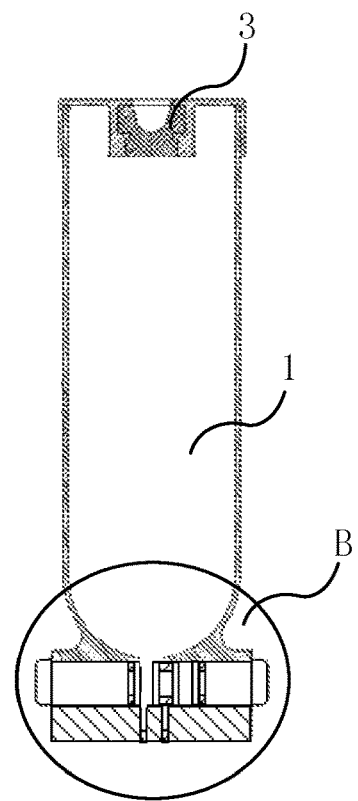
FIG. 3 is a schematic structural diagram of a centrifuge apparatus for separating blood components according to an embodiment of the present application.
Figure 4:
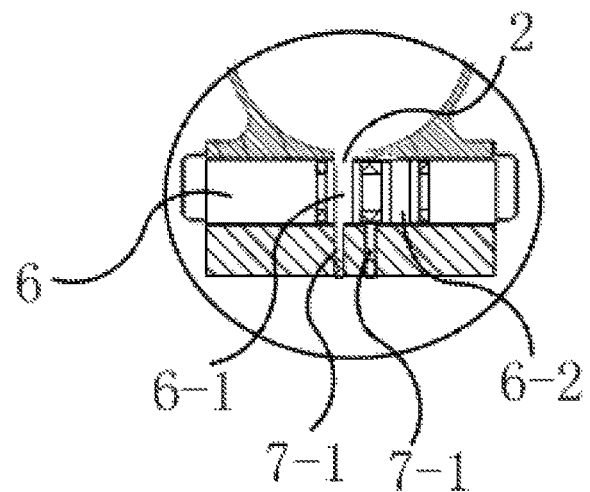
FIG. 4 is a partially enlarged diagram of a part B in FIG. 3.

A centrifuge apparatus for separating blood components involved in a third example is a variation of the first example, a schematic structural diagram thereof is shown in FIG. 3, and a partially enlarged diagram of a part B(that is, a flow dividing mechanism) in FIG. 3 is shown in FIG. 4. In a centrifuge apparatus provided in this example, structures of the centrifuge tube 1 and the halogenated butyl rubber plug 3 at the tube opening thereof are both similar to those in the first example, and the biggest difference from the first example is that the adjustable flow divider valve disposed in the flow dividing mechanism is a push-type or translatable flow divider valve, instead of a rotate-type or rotatable flow divider valve.

In the centrifuge apparatus of this example, the push-type flow divider valve is used to adjust relative positions of the discharge hole and the flow dividing channel. Specifically, the flow dividing mechanism includes a push-type flow divider valve 6, and a first flow guiding channel 6-1 and a second flow guiding channel 6-2 disposed in a valve body of the push-type flow divider valve 6. The rotate-type flow divider valve 6 is provided with a control hand wheel, and the push-type flow divider valve 6 may be pushed by operating the control hand wheel, so as to adjust respective positions of the first flow guiding channel 6-1 and the second flow guiding channel 6-2 relative to the discharge hole 2. Specifically, the push-type flow divider valve 6 may be in one of the following three directions: 1. the first flow guiding channel 6-1 and the second flow guiding channel 6-2 are both not in communicated with the discharge hole 2; 2. the first flow guiding channel 6-1 is in communication with the discharge hole 2; and 3. The second flow guiding channel 6-2 is in communication with the discharge hole 2.

Further, in this example, a first outlet 7-1 and a second outlet 7-2 are further provided. When the first flow guiding channel 6-1 is in communication with the discharge hole 2, the first outlet 7-1 is also in communication with the first flow guiding channel 6-1; thereby implementing communication between the discharge hole 2, the first flow guiding channel 6-1 and the first outlet 7-1. When the second flow guiding channel 6-2 is in communication with the discharge hole 2, the second outlet 7-2 is also in communication with the second flow guiding channel 6-2, thereby implementing communication between the discharge hole 2, the second flow guiding channel 6-2 and the second outlet 7-2. Therefore, the blood components at the bottom layer of the centrifuge tube 1 implement flow division by means of the discharge hole 2, the flow guiding channel and the outlet. During the actual use, bottom openings of the first outlet 7-1 and the second outlet 7-2 may be blocked respectively by using rubber plugs, and when flow division is conducted, the rubber plug is removed, and a receiving apparatus is additionally disposed under the outlet, thereby implementing receiving and storing of the blood component divided out.

A centrifuge apparatus for separating blood components involved in a fourth example is an improvement of the third example. Specifically, the centrifuge apparatus provided in this example is further provided with a limiting mechanism in the flow dividing mechanism, for example, a limiting guide shaft is disposed.

The limiting guide shaft conducts limiting and guiding on a pushing range of the push-type flow divider valve, and limits positions of the flow guiding channel and the discharge hole when the two are in communication with each other, thereby ensuring that, in the process of flow-dividing the blood component, the discharge hole and the flow guiding channel provide a stable flow-through channel, so that the manufacturing process of the PRP is more stable.

A centrifuge apparatus for separating blood components involved in a fifth example is another improvement of the third example. Specifically, a flow dividing cabin is additionally disposed in the third example and is used together with the push-type flow divider valve, so as to automatically implement collection of the blood component divided out. The flow dividing cabin may also be disposed in the centrifuge apparatus of the third example in a fixed manner or in a detachable manner. Moreover, the control hand wheel may be further provided with an isolating membrane, and the isolating membrane is used to isolate the hand of an operator from coming in direct contact with the hand wheel, thereby avoiding the hand from being contaminated by the blood sample during the operation.

A person of ordinary skill in the art can understand that the above mentioned implementation manners are specific examples to implement the present application. However, in actual applications, various changes may be made in forms and details without departing from the spirit and scope of the present application. For example, only one flow guiding channel is disposed in the centrifuge apparatus, the erythrocyte and the platelet-rich plasma are divided respectively from the same flow guiding channel, which may cause a slight mixing of the two blood components to slightly influence the purity and concentration of the prepared platelet-rich plasma; however, the objective of the present application may also be basically implemented, and therefore, this also falls within the protection scope of the present application.

What is claimed is:

1. A centrifuge apparatus for separating blood components, comprising:
  a centrifuge tube having a curved bottom contiguously connected to a cylindrical shaped sidewall of the centrifuge tube and extending across a lower end of the centrifuge tube, with a discharge hole extending through the curved bottom of the centrifuge tube;
  a flow dividing mechanism being fixed to an exterior of the curved bottom of the centrifuge tube;
  wherein the flow dividing mechanism comprises an outer encasement, and an adjustable flow divider valve received within an internal cavity of the flow dividing mechanism;

wherein the flow dividing mechanism further comprises first and second spaced apart outlets, and the adjustable flow divider valve comprises at least one flow guiding channel; and wherein the adjustable flow divider valve is moveable to selectively, alternatively, fluidically connect each of the first and second spaced apart outlets via the at least one flow guiding channel to the discharge hole for dividing two different blood components after centrifugation, respectively.

2. The centrifuge apparatus for separating blood components according to claim 1, further including a tube opening at an opposite end of the centrifuge tube than the discharge hole, wherein the tube opening includes a halogenated butyl rubber plug.

3. The centrifuge apparatus for separating blood components according to claim 1, wherein the adjustable flow divider valve comprises a rotatable flow divider valve, and the rotatable flow divider valve is rotatable in the flow dividing mechanism about an axis of the rotatable flow divider valve.

4. The centrifuge apparatus for separating blood components according to claim 1, wherein the at least one flow guiding channel comprises a first flow guiding channel and a second flow guiding channel that are spaced from each other; and wherein the adjustable flow divider valve is alternatively operable to fluidically connect the first of the spaced apart outlets via the first flow guiding channel to the discharge hole, and to fluidically connect the second of the spaced apart outlets via the second flow guiding channel to the discharge hole, respectively.

5. The centrifuge apparatus for separating blood components according to claim 4, wherein the flow dividing mechanism further comprises a first fluid storage chamber fluidically connected to the first of the outlets, and a second fluid storage chamber fluidically connected to the second of the outlets; and wherein when the first flow guiding channel is in fluid communication with the discharge hole, the first fluid storage chamber is in fluid communication with the first flow guiding channel; and, wherein when the second flow guiding channel is in fluid communication with the discharge hole, the second fluid storage chamber is in fluid communication with the second flow guiding channel.

6. The centrifuge apparatus for separating blood components according to claim 5, wherein the first fluid storage chamber and the second fluid storage chamber, each include a halogenated butyl rubber plug.

7. The centrifuge apparatus for separating blood components according to claim 1, wherein the adjustable flow divider comprises a push-type flow divider valve, and the flow divider valve is slideable in the flow dividing mechanism along a direction perpendicular to a longitudinal direction of the sidewall of the centrifuge tube.

8. The centrifuge apparatus for separating blood components according to claim 1, wherein the first and second spaced apart outlets of the flow dividing mechanism comprise diametrically opposed fluid outlets.

* * * * *